United States Patent [19]

Kohl

[11] 4,405,721
[45] Sep. 20, 1983

[54] DIAGNOSTIC AGENT FOR THE DETECTION OF KETONE BODIES

[75] Inventor: Helmut Kohl, Wetter, Fed. Rep. of Germany

[73] Assignee: Behringwerke Aktiengesellschaft, Marburg, Fed. Rep. of Germany

[21] Appl. No.: 246,057

[22] Filed: Mar. 20, 1981

[30] Foreign Application Priority Data

Mar. 22, 1980 [DE] Fed. Rep. of Germany ....... 3011168

[51] Int. Cl.$^3$ ................... G01N 33/16; G01N 33/48; G01N 33/64
[52] U.S. Cl. ......................................... 436/128; 436/8
[58] Field of Search ............................ 252/408, 408.1; 23/230 B, 230 R; 436/8, 14, 128

[56] References Cited

U.S. PATENT DOCUMENTS

| | | | |
|---|---|---|---|
| 2,283,262 | 5/1942 | Kamlet | 436/128 |
| 2,509,140 | 5/1950 | Free | 436/128 |
| 2,577,978 | 12/1951 | Nicholls et al. | 436/128 |
| 2,990,253 | 6/1961 | Smeby | 436/128 |
| 3,212,855 | 10/1965 | Mast et al. | 436/128 |
| 3,880,590 | 4/1975 | Ogawa et al. | 436/128 |
| 3,997,565 | 12/1976 | Kauer | 260/340.3 |
| 4,071,321 | 1/1978 | Lam | 252/408 |
| 4,097,240 | 6/1978 | Hirsch | 436/128 |
| 4,147,514 | 4/1979 | Magers et al. | 252/408 |
| 4,171,416 | 10/1979 | Motegi et al. | 526/245 |
| 4,184,850 | 1/1980 | Habenstein | 436/128 |
| 4,193,766 | 3/1980 | Davnora et al. | 23/230 R |

FOREIGN PATENT DOCUMENTS 56-141560 11/1981 Japan ................................. 436/128

OTHER PUBLICATIONS

Cram, Donald J., Science, vol. 219, No. 4589, pp. 1177-1183, "Cavitands: Organic Hosts with Enforced Cavities."

*Primary Examiner*—Brooks H. Hunt
*Assistant Examiner*—M. Moskowitz
*Attorney, Agent, or Firm*—Curtis, Morris & Safford

[57] ABSTRACT

Diagnostic agents containing sodium nitroprusside are storage-stabilized by the presence of a compound having one of the formulas $$N \underset{(CH_2)_{n2}-X_2-(CH_2)_{n2}}{\overset{(CH_2)_n-X-(CH_2)_n}{\underset{(CH_2)_{n1}-X_1-(CH_2)_{n1}}{\diagup}}} N \quad \text{or}$$

$$N \underset{(CH_2)_{n2}-X_2-(CH_2)_{n2}-Y_2-(CH_2)_{m2}}{\overset{(CH_2)_n-X-(CH_2)_n-Y-(CH_2)_m}{\underset{(CH_2)_{n1}-X_1-(CH_2)_{n1}-Y_1-(CH_2)_{m1}}{\diagup}}} N, \quad \text{or}$$

a cyclic compound of the formula $$A^1 \overset{A^2 \overset{A^3}{\frown}}{\underset{\smile}{\frown}} A^k$$

wherein each A has the formula $$-Z-\underset{R^2}{\overset{R^1}{\underset{|}{C}}}-\underset{R^4}{\overset{R^3}{\underset{|}{C}}}\left[\underset{R^6}{\overset{R^5}{\underset{|}{C}}}\right]_{z1}\left[-Z-\underset{R^8}{\overset{R^7}{\underset{|}{C}}}-\underset{R^{10}}{\overset{R^9}{\underset{|}{C}}}-(C)_{z2}\underset{R''}{\overset{R''}{\underset{|}{-}}}\right]_{z3},$$

wherein X and Y are oxygen or sulfur and Z is oxygen, sulfur, or NH.

12 Claims, No Drawings

DIAGNOSTIC AGENT FOR THE DETECTION OF KETONE BODIES

The present invention relates to a diagnostic agent for the detection of ketone bodies in fluids.

The detection of ketone bodies in urine is very important in the diagnosis and control of diabetics. This sensitive and rapid control in nowadays carried out with rapid diagnostic agents, for example urine test strips. The ketone detection is generally based on the Legal test, the concentration of the deep violet dyestuff obtained upon reaction of a ketone body with sodium nitroprusside being a measure of the quantity of the ketone body present.

The preparation of ketone test strips according to German Pat. No. 1,256,920 comprises a two-step procedure, which involves initially impregnating the papers with an aqueous buffer and an amino acid and subsequently applying the sodium nitroprusside indicator, in an organic solvent, to the preimpregnated papers.

This preparation method is necessary, since the indicator, which is no longer stable at a pH of more than 7, would decompose to form brown secondary products on contact with traces of water, for example in the form of atmospheric moisture. This brown coloration prevents a sensitive detection. Decomposition of the indicator may even result in a complete disappearance of the latter on the test paper.

German Pat. No. 1,256,920 proposes a stabilization of the indicator by separating the basic buffer and sodium nitroprusside from one another by means of a protective layer made of a film-forming compound. The papers obtained in this way are relatively stable, certainly. However, their reaction velocity and their sensitivity no longer correspond to the requirements imposed thereon. According to German Pat. Nos. 2,158,125 and 2,605,221, papers impregnated initially with the basic buffer are subsequently impregnated with a solution of sodium nitroprusside in methanol and an organic solvent miscible with methanol.

The papers thus obtained are brittle and have a tendency to fracture during their manufacture so that expensive reaction carriers may have to be used (German Pat. No. 2,158,124). The stability of these papers varies. A separation agent is also used with these papers to achieve a stabilizing effect. Suitable separation agents are the corresponding solvents miscible with methanol (German Pat. No. 2,605,221). According to German Offenlegungsschrift No. 2,733,426, basic buffer is first covered with an organic acid, for example oleic acid, and the indicator is applied in a third impregnation step. These papers, too, have a limited stability to storage and have to be processed, for example at a relative atmospheric humidity of below 40%, in order to prevent an immediate brown coloration thereof. This third impregnation step also gives brittle papers having a tendency to fracture. A further disadvantage is that a fixation of the papers on a carrier sheet by means of the usual bonding techniques is impaired by the considerable quantities of salts applied thereon.

The present invention was concerned with the problem of providing a stabilizer for a diagnostic agent useful in the detection of ketone bodies in fluids, which stabilizer would permit a preparation of ketone test papers without particular precaution, a prerequisite being that said papers are ready to process, stable to storage and characterized by the sensitivity required for their use.

This problem is solved in accordance with the present invention by providing a diagnostic agent useful in the detection of ketone bodies in fluids, which consists of a carrier matrix, that has been impregnated with a buffer, an amino acid and sodium nitroprusside in an organic solvent, said diagnostic agent being characterized by a content of a compound of formula I

wherein,
k is an integer of from 2 to 10 and an
A member represents the following structure

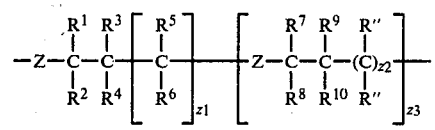

wherein
Z is oxygen, sulfur, or NH,
$R^1$, $R^2$, $R^5$, $R^6$, $R^7$, $R^8$, and $R''$ taken alone are hydrogen,
$R^3$, $R^4$, $R^9$, and $R^{10}$ taken alone are hydrogen or $C_1$–$C_3$ alkyl,
$R^1$ and $R^3$ taken together or $R^7$ and $R^9$ taken together are $-CH_2CH_2CH_2CH_2-$ or $-CH=CH-CH-CH-$,
$R^2$ and $R^4$ taken together and $R^8$ and $R^{10}$ taken together are a carbon-carbon bond,
$z_1$ and $z_2$ are each an integer from 0 to 4, and
$z_3$ is 0 or 1 but such that the compound

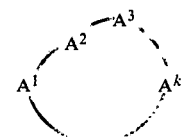

contains at least four Z atoms, and
wherein, when $z_1$ is 1, $R^5$, $R^6$, $R^7$, and $R^8$ taken together, in addition to their earlier definitions may be $=CH-CH=$, and
wherein, when $z_2$ and $z_3$ are each 1, both groups $R''$ of member $A^k$, taken together with $R^1$ and $R^2$ of adjacent member $A^{k-1}$, in addition to their earlier definitions may be $=CH-CH-$, whereby to form a ring, connecting members $A^k$ and $A^{k-1}$,

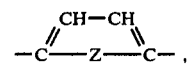

or a compound of the formula II

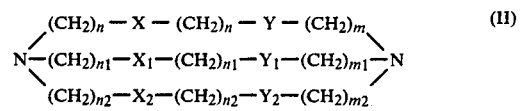

(II)

wherein
n, $n_1$ and $n_2$ each are 2 or 3,
m, $m_1$ and $m_2$ are an integer of from 0 to 3,
X, $X_1$, $X_2$, Y, $Y_1$ and $Y_2$ each are oxygen or sulfur or —Y—, —$Y_1$— and —$Y_2$— each represent a bond, in which case m, $m_1$ and $m_2$, respectively, are 0.

The stabilizing action of these compounds was surprising. It was still more astonishing that this stabilization also takes place when using compounds of formula I or II which are considered as being hygroscopic. This positive action of the compounds according to the invention is most pronounced when they are used in conjunction with sodium nitroprusside. It can also be observed, however, when water-soluble compounds of formula I or II are applied onto the carrier matrix together with the basic buffer. The quantity of stabilizer present in the ready-to-dip papers should be adapted to the corresponding quantity of indicator, although the absolute quantity is not critical. For example, the molar ratio of stabilizer to indicator may be in the range of from 0.1 to 15 mols per 1 mol of indicator. In general a limit of the quantity of stabilizer to be used is given only by the solubility of the latter in the solvent used in each case.

Preferred compounds of the formula I are those wherein X is oxygen or NH, $m_1$ and $m_2$ each are zero or 1, $R^5$ and $R^6$, in the case of $m_1$ being 1, each are hydrogen and the other symbols have the meanings given above.

Preferred compounds of the formula I are those wherein the symbols have the following meanings:
n is an integer of from 2 to 3,
X is oxygen,
$m_1$, $m_2$ are zero,
$R^1$-$R^4$ each are hydrogen,
$R^7$-$R^{10}$ each are hydrogen,
$R^1$ and $R^3$ together represent a CH=CH—CH=CH or $CH_2$—$CH_2$—$CH_2$—$CH_2$ group,
$R^2$ and $R^4$ together represent a bond and
m is zero or 1.

The following compounds are particularly preferred, the meanings of the symbols being given for part thereof and these compounds being obtained when applying the respective meanings of the symbols to the respective general formula:

12-crown-4;

15-crown-5 (formula I: n=3, X in all members is oxygen, $m_1$=$m_2$=zero or $R^1$-$R^4$ and $R^7$-$R^{10}$ each are hydrogen; m in two members is 1 and in one member is zero);

18-crown-6 (formula I: n=3; X in all members is oxygen, $m_1$=$m_2$=zero, m is $R^1$-$R^4$ and $R^7$-$R^{10}$ each are hydrogen);

Dibenzo-18-crown-6 (formula I: n=3; X in all A members is oxygen, $m_1$=$m_2$=zero, m=1; $R^1$ and $R^3$ in $A^1$ represent together a CH=CH—CH=CH group and —$R^2$ and —$R^4$ form together a bond and $R^7$-$R^{10}$ each are hydrogen; $R^1$-$R^4$ in $A^2$ each are hydrogen, $R^7$ and $R^9$ represent together a CH=CH—CH=CH group and —$R^8$ and —$R^{10}$ represent together a bond; $R^1$-$R^4$ and $R^7$-$R^{10}$ in $A^3$ each are hydrogen);

Dicyclohexano-18-crown-6;

1,4,7,10,13,16 -Hexaaza-cyclooctadecane trisulfate; and

Compounds of the Kryptofix ® series of Merck, for example Kryptofix 222 (i.e. 4, 7, 13, 16, 21, 24-hexaoxa-1,10-diazabicyclo-[8,8,8]-hexacosane), Kryptofix 211 (i.e. 4, 7, 13, 16, 21-pentaoxa-1,10-diazabicyclo-[8,8,5]-tricosane), and Kryptofix 221 (i.e. 4, 7, 13, 18-tetraoxa-1,10-diazabicyclo-[8,5,5]-eicosane) (compounds of the formula II, wherein n, $n_1$, $n_2$, m, $m_1$ and $m_2$ each represent the integer 2 and X, $X_1$, $X_2$, Y, $Y_1$ and $Y_2$ each represent oxygen or n, $n_1$, $n_2$ and $m_2$ represent the integer 2, m and $m_1$ each are zero and X, $X_1$, $X_2$ and $Y_2$ each are oxygen and —Y— and —$Y_1$— represent a bond or n, $n_1$,$n_2$,$m_1$ and $m_2$ each represent the integer 2, m is zero and X, $X_1$, $X_2$, $Y_1$ and $Y_2$ each represent oxygen and —Y— represents a bond).

Particular suitable are stable compounds such as dibenzo-18-crown-6 or 18-crown-6.

A molar ratio of from 0.5 mol to 1.5 mols of stabilizer to 1 mol of indicator is preferred, if the stabilizer is applied in the form of a solution in an organic solvent. When applying the stabilizer together with the buffer, the molar quantity of the stabilizer should be in the range of from 7 to 12.

It has been further found that a solid organic carboxylic acid can be additionally added to the organic solution.

The ketone papers prepared with the use of said stabilizers are white. They are therefore suitable for detecting even traces of ketone bodies. For example the sensitivity limit for acetoacetic acid is within the range of from 3 to 4 mg/dl so that physiological quantities of acetoacetic acid can just no longer be recorded. The stability of the papers is very good. They do not lose their white coloration during 48 hours' storage at room temperature and a relative atmospheric humidity of 60%. As compared thereto, papers obtained according to German Pat. No. 2,148,125 exhibit a pronounced color change after 60 minutes when kept under identical conditions. The stabilized papers may be manufactured without particular precaution. They are elastic and do not break.

The following examples serve to illustrate the present invention:

EXAMPLE 1

Impregnation solution 1:
80 g of glycine,
17 g of sodium hydroxide,
100 ml of water.
The pH is adjusted to 10.0.
Impregnation solution 2:
1 g of sodium nitroprusside,
1.6 g of 18-crown-6,
40 ml of methanol,
20 ml of dimethyl formamide.

Paper of the type Schleicher and Schüll 2316 is treated with the impregnation solution 1 and subsequently dried at 80° C. until it has a residual moisture of less than 3%. Upon the second impregnation step, a colorless paper which has the above-described positive properties is obtained.

EXAMPLE 2

Impregnation solution 1: according to Example 1.
Impregnation solution 2:
0.5 g of sodium nitroprusside,
0.3 g of dibenzo-18-crown-6,
40 ml of methanol,
20 ml of propanol.

The papers are prepared according to Example 1. These papers, too, are particularly stable to storage.

EXAMPLE 3

Example 2 is repeated, except that 3 g of citric acid are additionally added to the organic solvent. A stable paper is again obtained.

EXAMPLE 4

Impregnation solution 1:
80 g of glycine,
17 g of sodium hydroxide,
2.5 g of Kryptofix ® 222, (Merck 10647)
100 ml of water.
The pH is adjusted to 10.0
Impregnation solution 2:
0.5 g of sodium nitroprusside,
1.0 g of citric acid,
40 ml of methanol,
20 ml of propanol.

This paper is likewise distinguished by the above-described advantages properties.

What is claimed is:

1. A diagnostic agent for the detection of ketone bodies, said agent comprising a carrier impregnated with a buffer, an amino acid, sodium nitroprusside, and a stabilizing compound selected from the group consisting of compounds of the formulas

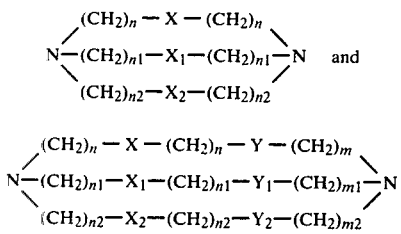

wherein
n, $n_1$ and $n_2$ each are 2 or 3,
m, $m_1$ and $m_2$ each are an integer from 0 to 3, and
X, $X_1$, $X_2$, Y, $Y_1$, $Y_2$ each are oxygen or sulfur, and
(III) a cyclic compound of the formula

wherein
k is an integer from 2 to 10,
each A has the formula

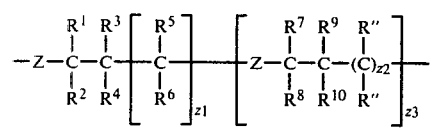

wherein
Z is oxygen, sulfur, or NH,
$R^1$, $R^2$, $R^5$, $R^6$, $R^7$, $R^8$, and $R''$ taken alone are hydrogen,
$R^3$, $R^4$, $R^9$, and $R^{10}$ taken alone are hydrogen or $C_1$–$C_3$ alkyl, $R^1$ and $R^3$ taken together or $R^7$ and $R^9$ taken together are —$CH_2CH_2CH_2CH_2$— or —CH=CH—CH=CH—,
$R^2$ and $R^4$ taken together and $R^8$ and $R^{10}$ taken together are a carbon-carbon bond,
$z_1$ and $z_2$ are each an integer from 0 to 4, and
$z_3$ is 0 or 1 but such that the compound

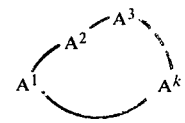

contains at least four Z atoms, and
wherein, when $z_1$ is 1, $R^5$, $R^6$, $R^7$, and $R^8$ taken together, in addition to their earlier definitions may be =CH—CH=, and
wherein, when $z_2$ and $z_3$ are each 1, both groups $R''$ of member $A^k$, taken together with $R^1$ and $R^2$ of adjacent member $A^{k-1}$, in addition to their earlier definitions may be =CH—CH—, whereby to form a ring, connecting members $A^k$ and $A^{k-1}$, of the formula

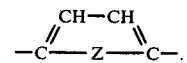

2. A diagnostic agent as in claim 1 wherein said stabilizing compound has formula (I) of Claim 1.

3. A diagnostic agent as in claim 1 wherein said stabilizing compound has formula (II) of Claim 1.

4. A diagnostic agent as in claim 1 wherein said stabilizing compound has formula (III) of Claim 1.

5. A diagnostic agent as in claim 4 wherein
k is 2 or 3,
Z is oxygen,
$z_1$ and $z_2$ are each zero,
$z_3$ is zero or 1, and
$R^1$–$R^4$ and $R^7$–$R^{10}$ are each hydrogen.

6. A diagnostic agent as in claim 4 wherein
k is 2 or 3,
Z is oxygen,
$z_1$ and $z_2$ are each zero, $z_3$ is zero or 1,
$R^7$–$R^{10}$ are each hydrogen,
$R^1$ and $R^3$, taken together, are
—CH=CH—CH=CH— or
—$CH_2$—$CH_2$—$CH_2$—$CH_2$— and
$R^2$ and $R^4$, taken together, are a carbon-carbon bond.

7. A diagnostic agent as in claim 1 wherein said stabilizing agent is a crown ether.

8. A diagnostic agent as in claim 7 wherein said crown ether is 12-crown-4, 15-crown-5, 18-crown-6, dibenzo-18-crown-6, or dicyclohexano-18-crown-6.

9. A diagnostic agent as in claim 8 wherein said crown ether is 18-crown-6.

10. A diagnostic agent as in claim 10 wherein said crown ether is dibenzo-18-crown-6.

11. A diagnostic agent as in claim 1 wherein said stabilizing agent is 1, 4, 7, 10, 13, 16-hexaza-cyclooctadecane trisulfate.

12. A diagnostic agent as in claim 1 wherein said stabilizing agent is 4, 7, 13, 16, 21, 24-hexaoxa-1, 10-diazabicyclo-[8,8,8]-hexacosane, 4, 7, 13, 16, 21-pentaoxa-1, 10-diazabicyclo-[8,8,5]-tricosane, or 4, 7, 13, 18-tetraoxa-1, 10-diazabicyclo-[8,8,5]-eicosane.

* * * * *